(12) United States Patent
Tedesco et al.

(10) Patent No.: US 6,351,306 B1
(45) Date of Patent: Feb. 26, 2002

(54) OPTICAL MEASUREMENT PROBE CALIBRATION CONFIGURATIONS

(75) Inventors: James M. Tedesco, Livonia; Joseph B. Slater, Dexter, both of MI (US)

(73) Assignee: Kaiser Optical Systems, Inc., Ann Arbor, MI (US)

( * ) Notice: Subject to any disclaimer, the term of this patent is extended or adjusted under 35 U.S.C. 154(b) by 0 days.

(21) Appl. No.: 09/420,483

(22) Filed: Oct. 19, 1999

(51) Int. Cl.[7] .......................... G01N 3/44; G01N 21/64; G01N 21/65
(52) U.S. Cl. .................... 356/301; 356/318; 250/458.1
(58) Field of Search ................................. 256/304, 311, 256/313, 315, 316, 317, 318, 417; 250/458.1, 459.1, 461.1, 461.2

(56) References Cited

U.S. PATENT DOCUMENTS

| | | | |
|---|---|---|---|
| 5,285,071 A | 2/1994 | LaCount | 250/343 |
| 5,341,206 A | 8/1994 | Pittaro et al. | 356/301 |
| 5,452,084 A | 9/1995 | Mitchell et al. | 356/301 |
| 5,452,723 A | 9/1995 | Wu et al. | 128/664 |
| 5,638,173 A | 6/1997 | Smith et al. | 356/301 |
| 5,792,049 A | 8/1998 | Eppstein et al. | 600/306 |
| 5,850,623 A | 12/1998 | Carman, Jr. et al. | 702/28 |
| 5,902,245 A | 5/1999 | McHenry et al. | 600/476 |
| 5,933,792 A | 8/1999 | Andersen et al. | 702/32 |
| 5,956,138 A | 9/1999 | Slater | 356/318 |
| 6,002,990 A | 12/1999 | Hanna | 702/88 |
| 6,067,156 A | * 5/2000 | Slater et al. | 356/301 |
| 6,141,095 A | * 10/2000 | Allen et al. | 356/301 |

* cited by examiner

*Primary Examiner*—F. L Evans
(74) *Attorney, Agent, or Firm*—Gifford, Krass, Groh, Sprinkle, Anderson & Citkowski, PC

(57) ABSTRACT

Methods and apparatus are disclosed for calibrating remote optical probe configurations of the type wherein a spectrum emitted by a sample is delivered to a spectrograph for analysis using fluorescence, Raman detection or other dispersive techniques. The invention may be used to calibrate the spectrograph wavelength axis, the system spectral response or intensity axis, and the wavelength of the laser used for excitation. A collection optical fiber having a first end for receiving wavelengths emitted by the sample has a second end for delivering the wavelengths to a base unit containing the spectrograph. A calibration optical fiber is used to deliver an optical calibration signal to a point proximate to the first end of the collection optical fiber, and an optical element is used to direct the optical calibration signal into the collection optical fiber so that the spectrograph receives both the wavelengths emitted by the sample and the optical calibration signal. A neon reference lamp is preferably used to calibrate the spectrograph wavelength axis, and a tungsten halogen lamp is employed to calibrate the system spectral response or intensity axis. The invention is applicable to a variety of configurations, including process monitoring environments utilizing a plurality of probeheads. To calibrate the laser wavelength, one of the probeheads may be assigned to receiving wavelengths emitted by a reference substance such as cyclohexane.

35 Claims, 4 Drawing Sheets

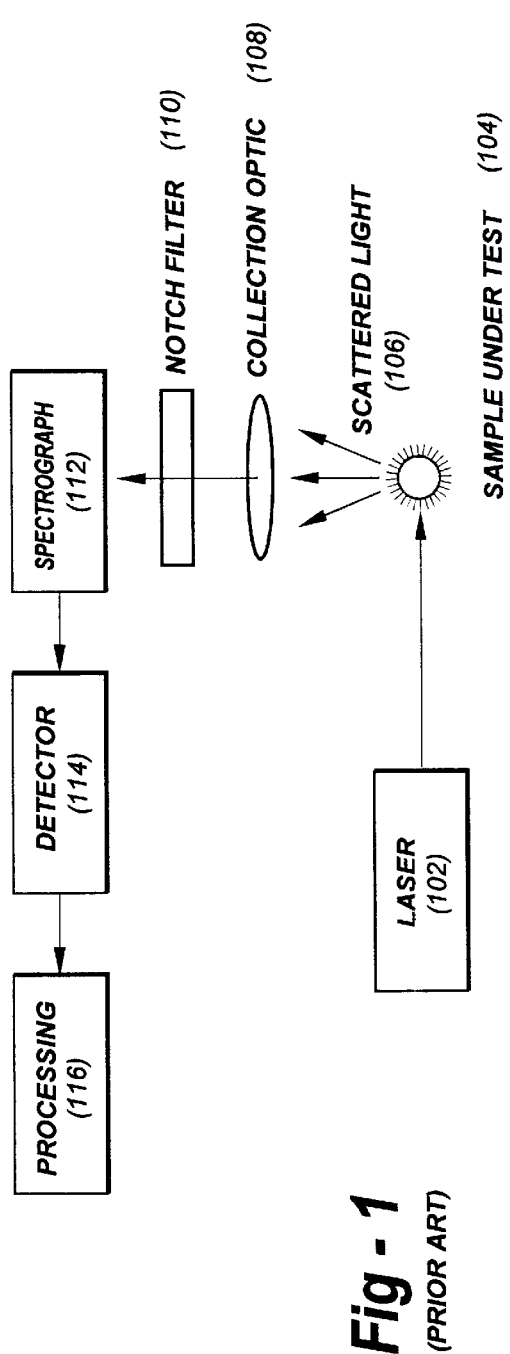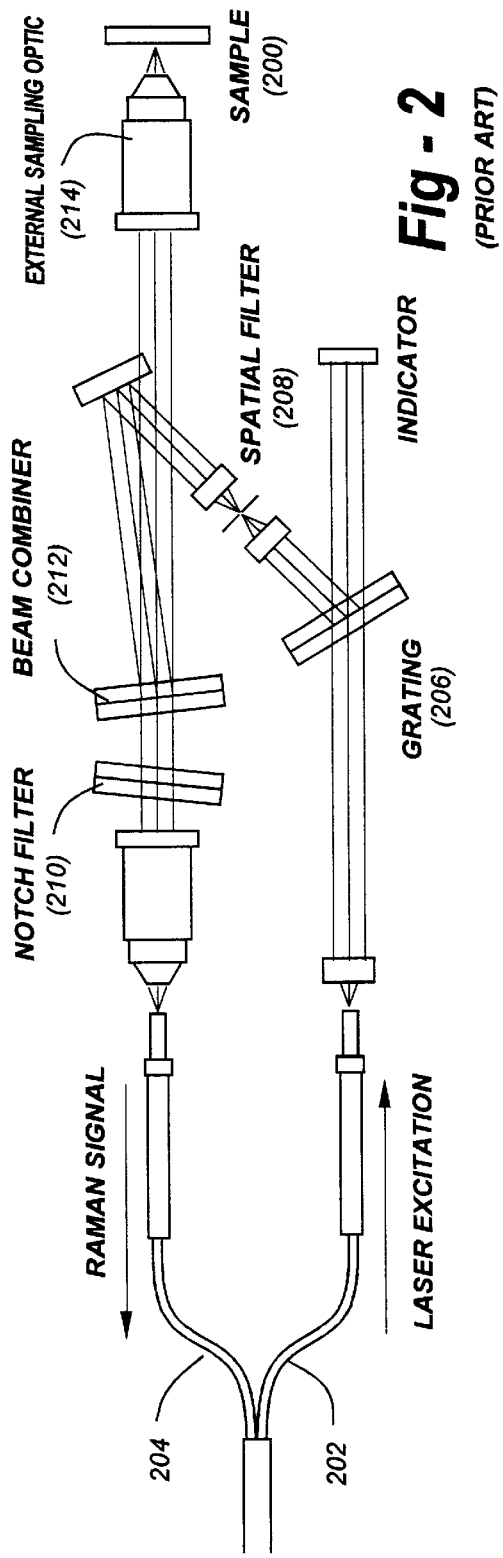
Fig-1 (PRIOR ART)
Fig-2 (PRIOR ART)

OPTICAL MEASUREMENT PROBE CALIBRATION CONFIGURATIONS

FIELD OF THE INVENTION

This invention relates generally to induced radiative effects such as Raman and fluorescence detection and, in particular, to methods and apparatus for automatically calibrating wavelength and intensity aspects of such a system.

BACKGROUND OF THE INVENTION

Raman spectroscopy is gaining increasing acceptance in on-line process monitoring, due in large part to developments in instrumentation and associated component technologies. For a number of process applications, Raman analyzers have demonstrated significant advantages over alternative techniques such as gas chromatography, IR spectroscopy, and NIR spectroscopy. As a non-destructive, real-time technique, Raman spectroscopy is compatible with a wide variety of samples including opaque solids, aqueous solutions, emulsions, and gases, without the need for sample preparation.

The basic building blocks of a Raman instrument are shown in FIG. 1. An excitation laser 102 illuminates a sample under test 104. Scattered light 106 is collected by optic(s) 108. A notch filter 110 is typically used to remove the strong Rayleigh (unshifted) component that would otherwise hide the weak Raman signal. A spectrograph 112 spectrally separates the remaining Raman signal, which is then fed to a detector 114 coupled to processing hardware and software 116.

Sampling in a process environment is most conveniently accomplished using a probehead assembly, as shown in the prior-art system of FIG. 2. Delivery of the excitation laser beam to the sample under test 200 is accomplished via an excitation fiber-optic cable 202. Scattered light from the sample is collected by the probehead and routed back to the analyzer via a separate collection fiber-optic cable 204.

Typical process installations may run hundreds of meters of fiber cable between the analyzer and probehead. Each optical fiber has its own Raman and luminescence signatures, which must be removed at the probehead before the laser illumination is delivered to the sample. Similarly, the strong laser Rayleigh line must be removed from the collected frequency-shifted scatter at the probehead before entering the return fiber; otherwise, it may generate a competing fiber signature on the way back to the analyzer. A holographic grating 206 and spatial filter 208 are therefore inserted into the beam delivery path to remove the fiber signature. The Rayleigh line is removed from the collected Raman scatter by a holographic notch filter 210 in the collection path. A holographic beam combiner 212 serves to combine the laser beam delivery path onto a common optical axis with the collection path, so that a common sampling optic 214 may be used for both paths.

As shown in FIG. 3, modern Raman instruments may also be configured to monitor multiple sample points in a process. In a typical industrial installation, multiple remote probeheads 302 are coupled to a central instrument 304 via fiber optic cables 306. The central instrument 304 typically houses a laser source 310, spectrograph 312, CCD detector 314 and control electronics 316. A sequencer or splitter 320 is used to multiplex the output of the laser source 310.

Widespread acceptance of Raman spectroscopy in chemical process monitoring requires accurate and timely instrument calibration. The three key parameters to be calibrated in a Raman analyzer are: 1) the spectrograph wavelength axis; 2) the system spectral response or intensity axis; and 3) the laser wavelength itself.

Wavelength Calibration

Wavelength calibration determines the wavelength versus pixel mapping function of the spectrograph/camera assembly. There are a number of known wavelength calibration sources applicable to Raman spectrometers. Atomic emission lines from readily available neon or argon lamps form convenient wavelength calibration sources. Neon is preferable in that it provides emission lines in close proximity to the common 785 nm and 532 nm laser lines used in process Raman. A neon emission can also provide reference lines near both edges of the CCD for gratings used in certain types of commercially available Raman analyzer equipment.

Wavelength calibration for later use in Raman data analysis is most accurate if the calibration signal is fed into the spectrograph via the same optical path that is used to collect Raman data. In addition, two factors make this impractical in the process environment. First, it is impractical to insert a neon lamp into the process pipeline; second, it is inconvenient to remove the probehead from the pipeline so that a calibration source may be placed in the collection path.

In addition, because Raman detection is a frequency-shift phenomenon, wavelength calibration of the spectrograph alone is not sufficient for analyzing Raman shifts with the greatest possible accuracy. Calibrating the wavelength or frequency of the excitation laser source is equally critical. While gas lasers such as helium-neon or argon-ion lasers emit precisely known atomic emission lines, the emission wavelengths of the solid-state lasers more common in process Raman are less stable, and therefore require frequent wavelength calibration.

Intensity Calibration

Intensity calibration determines the spectral response of the entire light collection path from the probe sampling optic to the CCD camera output signal. Intensity calibration in Raman spectroscopy is normally concerned with the relative spectral response of the system across its spectral range, rather than its absolute response. This is because sample composition or structure is normally determined from the shape of the Raman spectrum, such as band ratios, rather than an absolute response such as absorbance.

The purpose of intensity calibration is to correct the shape of the measured Raman spectrum. Factors that distort the shape of the spectrum as measured by the CCD include the spectral transmission of the optical elements, the spectral efficiency of the diffraction grating, the silicon quantum efficiency curve of the CCD detector elements, and pixel-to-pixel variations in CCD detector responsivity. By imaging a light source of known spectral output through the complete light collection path of the analyzer, all of these factors may be accounted for simultaneously.

In summary, although accurate laboratory calibration may be performed using external wavelength and intensity reference lamps, this approach requires access within or near the probehead assembly, which may impractical or unwarranted in a process environment. Although such access is not required when using internal calibration, existing techniques do not calibrate the intensity axis, and accuracy suffers because the actual optical collection path from a real sample is not used. The need therefore remains for a calibration arrangement which is conducive to automated, internal referencing while, at the same time, utilizes as much of the actual collection path as possible to enhance the accuracy of the system. A candidate configuration should feature an accuracy approaching that of the ideal laboratory protocol, without requiring lamps or electrical power at the process location.

SUMMARY OF THE INVENTION

This invention resides in methods and apparatus for calibrating remote optical probe configurations of the type wherein a spectrum emitted by a sample is delivered to a spectrograph for analysis. The teachings are applicable to various spectroscopic techniques, including fluorescence and Raman detection. Depending upon the embodiment, the system and processes may be used to calibrate the spectrograph wavelength axis, the system spectral response or intensity axis, and the wavelength of the laser used for excitation.

The preferred embodiment includes a collection optical fiber having a first end for receiving wavelengths emitted by the sample and a second end for delivering the wavelengths to a base unit containing the spectrograph. A calibration optical fiber is used to deliver an optical calibration signal to a point proximate to the first end of the collection optical fiber, and an optical element is used to direct the optical calibration signal into the collection optical fiber so that the optical analysis means receives both the wavelengths emitted by the sample and the optical calibration signal.

A neon reference lamp is preferably used to calibrate the spectrograph wavelength axis, whereas a tungsten halogen lamp is employed to calibrate the system spectral response or intensity axis. The wavelength of the excitation laser may also be calibrated using a known Raman scattering line of a standard material. The neon lamp may be placed directly against the calibration fiber such that the glowing neon gas emission will be directly in front of the fiber end. The tungsten halogen lamp is preferably used in a lensed configuration, such that the light is focussed through the neon lamp envelope onto the calibration fiber end. In the preferred embodiment, the laser and reference lamp or lamps are disposed at the same location as the base unit to simplify fiber routing.

The invention is applicable to a variety of configurations, including process monitoring environments in which a plurality of probeheads and collection optical fibers are used, each one being associated with a different sample or portion thereof. A plurality of calibration optical fibers are also used in such a case, each having one end for delivering calibration signals to each probehead assembly. To calibrate the laser wavelength, one of the probeheads may be assigned to receiving wavelengths emitted by a reference substance such as cyclohexane.

BRIEF DESCRIPITON OF THE DRAWINGS

FIG. 1 is a drawing which shows the basic building blocks of a Raman instrument;

FIG. 2 illustrates the optical configuration of a representative probehead;

DETAILED DESCRIPTION OF THE INVENTION

Figure 4:
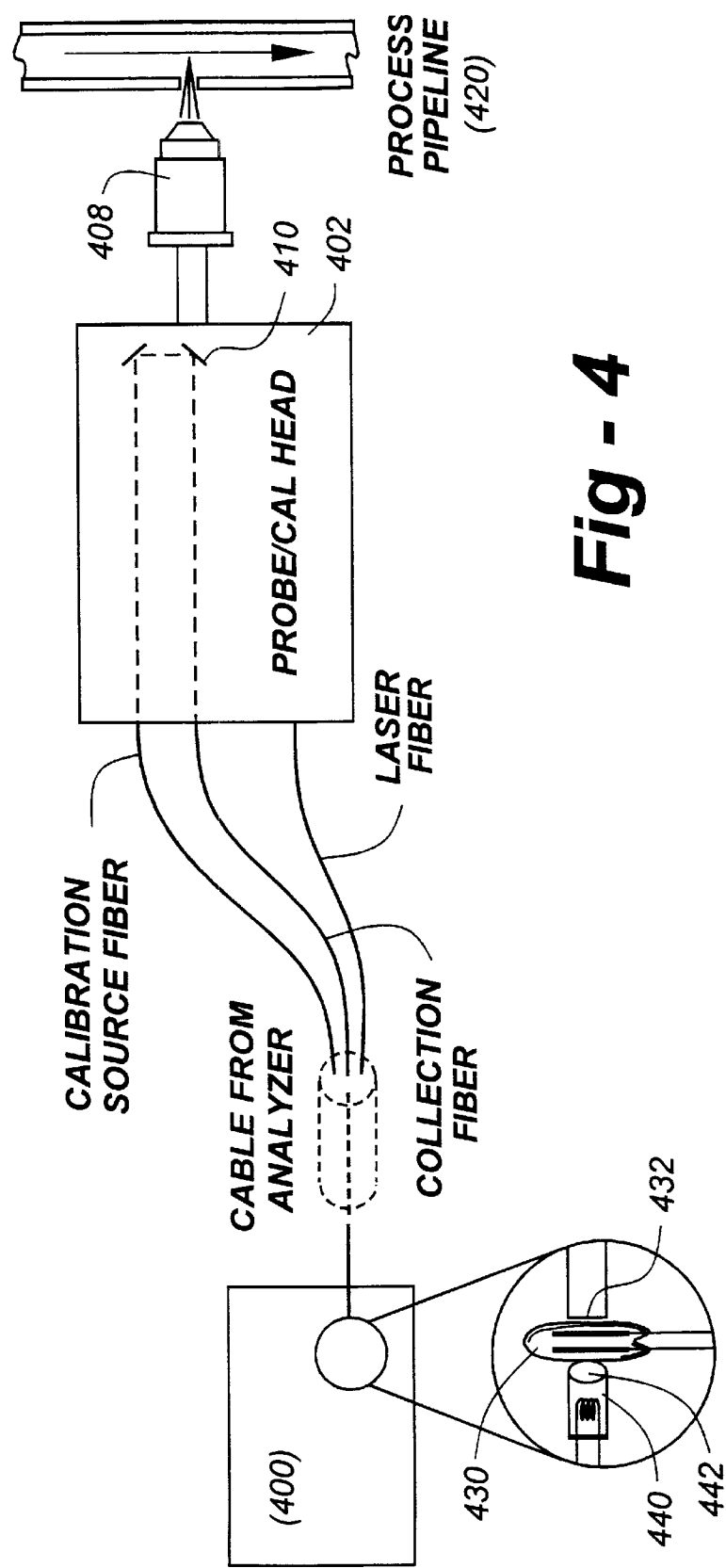
FIG. 4 is a schematic process analyzer and probehead arrangement according to the invention.

A system according to the invention is shown in FIG. 4. Calibration light is passed from a central analyzer 400 to a probehead assembly 402 through an auxiliary calibration optical fiber 406. The calibration signal is injected into the probehead collection path just inside the probehead sampling optic lens 408 using a beam combiner 410. As such, calibration may be performed without evacuating the process pipeline 420, and no electrical power is required at the sample point.

The system is capable of automated, on-line calibration with improved accuracy in both the wavelength and intensity axes, particularly if separate optical sources are employed for different purposes. In terms of wavelength calibration, any suitable reference lamp may be used, such as argon or neon, though the latter is preferred for reasons discussed elsewhere herein. The neon lamp 430 is preferably placed directly against the calibration optical fiber 406, such that the glowing neon gas emission will be directly in front of the fiber input end 432. Note that the probe-injected wavelength calibration path is optically equivalent to the ideal external path for purposes of wavelength calibration, since it is fed to the analyzer through the same optical fiber.

The light source for intensity calibration must be broadband, filling the entire spectral measuring range of the Raman analyzer with no gaps. The spectral output of the calibration light source must also be traceable to an industry-accepted standard. Fortunately, tungsten-halogen lamps offer a readily available source of reliable, repeatable spectral output. Miniature tungsten-halogen lamps, suitable for deployment in portable equipment, have negligible change in spectral shape over hundreds or even thousands of hours when driven by an accurately controlled current source. Such lamps also feature a sufficiently high color temperature (e.g. 2800 K) affording an ample signal across the entire measuring range of both visible and NIR Raman analyzers.

An off-the-shelf tungsten halogen lamp 440 is preferably used in a lensed configuration, such that the light is focussed through the neon lamp envelope onto the fiber end 432. An integral lens 442 may conveniently be employed for this purpose. Using this technique, both wavelength and intensity reference light is injected into the same fiber 406. The neon and halogen lamps may be separately turned on and off for independent calibration of both the wavelength and intensity axes.

With respect to intensity calibration, the technique is not as accurate as a comprehensive external calibration protocol. One reason is that window fouling is still a possible source of intensity calibration error since the sampling window is not included in the external calibration path. However, there exist several well-known techniques to minimize window fouling. For example, management of the window temperature, such as with a steam-jacket, has been effective in some applications. Other installations have used active window cleaning devices. In addition, although not as accurate as an ideal external calibration protocol, the inventive approach tracks shifts from an original external calibration with better accuracy than that achievable with calibration paths which are purely internal to the analyzer base unit.

Intensity calibration accuracy would also be affected by changes in the spectral transmission of the fiber optical path between the calibration lamps 430 and 440 in the central analyzer 400 and the probehead 402. However, under normal operating conditions, it may be assumed that this path, as well as the probehead sampling optic, are sufficiently spectrally stable. To compensate for not including the sampling optic in the automated calibration path, however, a one-time reference calibration between the automated hardware and a true external calibration should preferably be performed upon installation.

Figure 3:
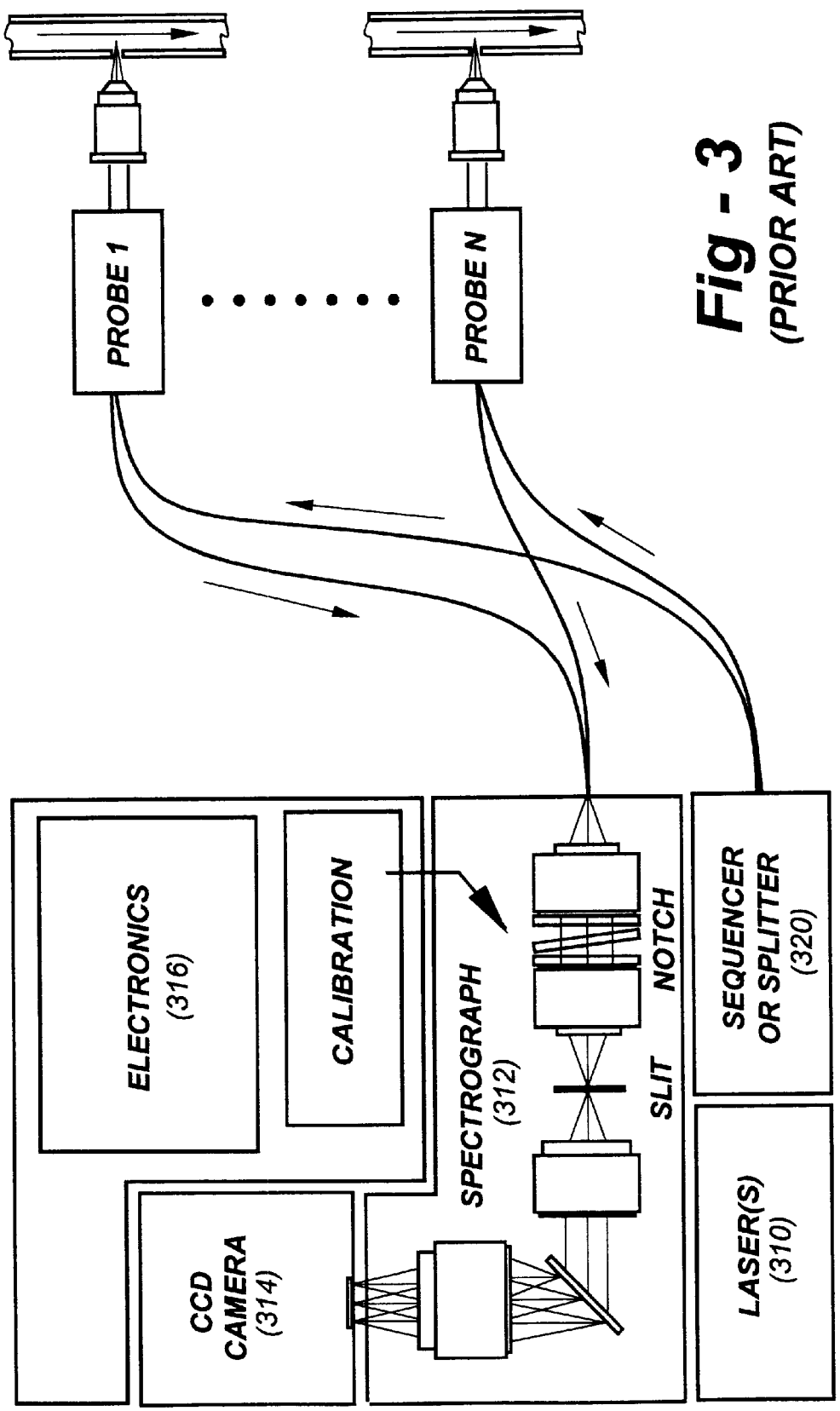
FIG. 3 illustrates how a Raman instrument may be configured to simultaneously multiple sample points in a process environment.

In the case of a system with multiple probes, as illustrated in FIG. 3, a separate calibration fiber is preferably used to carry the calibration light to each probe (not shown in FIG. 3). The calibration signal for each probe is preferably generated by a separate neon and tungsten halogen lamp pair. However, it would also be clear to one skilled in the art that other arrangements are possible, such as splitting the output from a single neon-tungsten lamp pair to serve all of the calibration fibers. Another approach would be to switch the output from a single neon-tungsten lamp pair to each calibration fiber in sequence or as needed.

Figure 5:
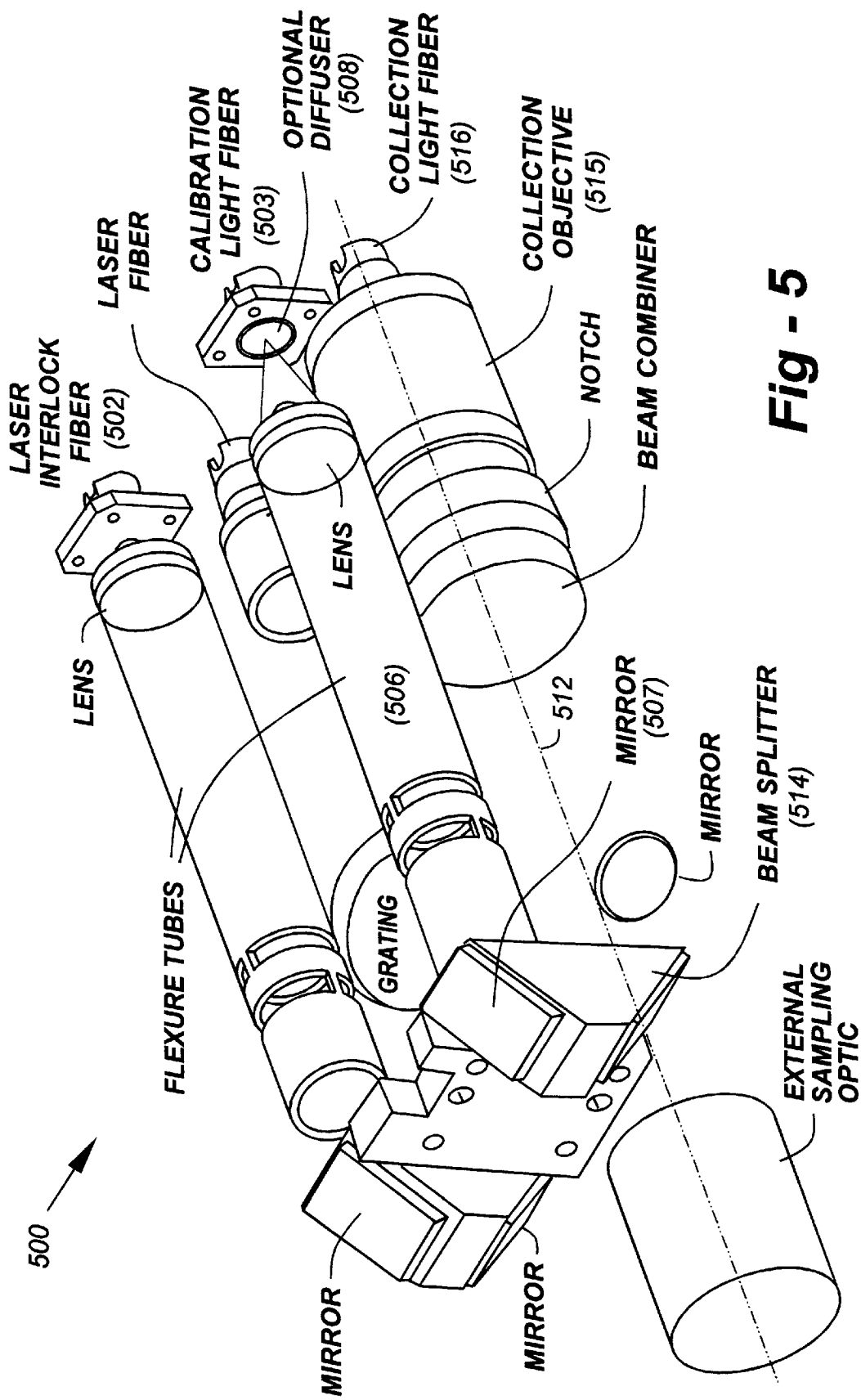
FIG. 5 is a drawing which illustrates probehead components according to a preferred embodiment.

FIG. 5 shows generally at 500 a more specific probehead implementation including portions of the invention. The depicted embodiment has two additional fiber-optic connectors, one (502) to accept a fiber containing a laser interlock signal (as disclosed in commonly assigned U.S. patent application Ser. No. 09/289,442) and a second fiber (503) that carries wavelength and/or intensity calibration reference light from lamps located at the base unit (not shown).

Calibration light is collimated by a lens 504 mounted in a flexure tube 506 for adjustment by externally accessible set screws (not shown). A diffuser 508 may optionally be employed. The collimated calibration light is folded at the end of the probehead by a mirror 507, and then directed into the collection path 512 of the probehead by a beamsplitter 514 that passes most of the collected Raman light and reflects a small amount of the calibration light. Since there is ample calibration light, some may be discarded without affecting performance.

The same lens 515 that focuses the Raman light into the collection fiber also focuses the calibration light into the collection fiber 516. The calibration light passes through the entire Raman collection optical path with the exception of the external probehead sampling optic which, as previously discussed, should have stable and relatively neutral spectral transmission characteristics.

In addition to the wavelength and intensity axes of the spectrograph, a calibration protocol is preferably employed to accurately calibrate the third critical parameter of a Raman analyzer, namely, the operating wavelength of the excitation laser. This is an indirect laser calibration that may use a known Raman scattering line of a standard material such as cyclohexane.

In a multi-channel system of the type shown in FIG. 3, one channel may be allocated to the Raman standard for laser wavelength calibration. Due to the strong signal available from such a material, a simple two-fiber, non-imaging probe may be used. This configuration allows absolute calibration of the laser line without reliance on an internal laser tracking signal. The arrangement provides totally automated wavelength axis calibration with accuracy fully equivalent to that of the ideal calibration protocol. Such a level of calibration refinement may be required in cases where particularly sensitive multivariate PLS process models must be accommodated.

We claim:

1. Calibrated optical measurement instrumentation for use in analyzing a sample with spectral analysis means, the instrumentation comprising:
   a collection optical fiber having a first end for receiving wavelengths emitted by the sample and a second end for delivering the wavelengths to the spectral analysis means;
   a source of an optical calibration signal;
   a calibration optical fiber for delivering the optical calibration signal to a point proximate to the first end of the collection optical fiber; and
   an optical element for directing the optical calibration signal into the collection optical fiber so that the optical analysis means receives both the wavelengths emitted by the sample and the optical calibration signal.

2. The instrumentation of claim 1, wherein the source of the optical calibration signal is disposed at the same location as the spectral analysis means.

3. The instrumentation of claim 1, wherein the wavelengths emitted by the sample are characteristic of Raman scattering.

4. The instrumentation of claim 1, wherein the wavelengths emitted by the sample are characteristic of fluorescence.

5. The instrumentation of claim 1, wherein the optical calibration signal includes discrete reference wavelengths for wavelength calibration.

6. The instrumentation of claim 5, wherein a neon lamp provides the reference wavelengths.

7. The instrumentation of claim 1, wherein the optical calibration signal includes a continuous reference intensity spectrum.

8. The instrumentation of claim 7, wherein a tungsten-halogen lamp provides the reference intensity spectrum.

9. The instrumentation of claim 1, wherein the optical calibration signal includes reference wavelengths and reference intensity spectra.

10. The instrumentation of claim 1, further including:
    a source of excitation radiation; and
    an excitation optical fiber for delivering the excitation radiation to the sample causing the wavelengths to be emitted by the sample.

11. The instrumentation of claim 1, further including:
    a plurality of collection optical fibers, each associated with a different sample or portion thereof; and
    a plurality of calibration optical fibers, each having one end for receiving the calibration signal.

12. The instrumentation of claim 1, further including:
    a laser having a wavelength to illuminate the sample; and
    a plurality of collection optical fibers, with one or more being associated with the sample and one or more receiving wavelengths scattered by a reference substance used to calibrate the laser.

13. The instrumentation of claim 12, wherein the substance used to calibrate the laser wavelength is cyclohexane.

14. Calibrated optical measurement instrumentation, comprising:
    spectral analysis means;
    a probehead assembly disposed remotely from the spectral analysis means;
    a source of excitation radiation;
    an excitation optical fiber for delivering the excitation radiation to the probehead assembly, the probehead assembly including one or more optical elements for directing the excitation radiation onto a sample so as to induce a spectral emission therefrom;
    a collection optical fiber for delivering the spectral emission from the sample to the spectral analysis means;
    a source of an optical calibration signal; and
    a calibration optical fiber for delivering the optical calibration signal to the probehead assembly, the probehead assembly including one or more optical elements for directing the optical calibration signal into the collection optical fiber, thereby enabling the spectral analysis means to analyze the spectral emission as a function of the optical calibration signal.

15. The instrumentation of claim 14, wherein the source of the optical calibration signal is disposed at the same location as the spectral analysis means.

16. The instrumentation of claim 14, wherein the spectral emission represents Raman scattering.

17. The instrumentation of claim 14, wherein the spectral emission represents fluorescence.

18. The instrumentation of claim 14, wherein the optical calibration signal includes discrete reference wavelengths for wavelength calibration.

19. The instrumentation of claim 18, wherein a neon lamp provides the reference wavelengths.

20. The instrumentation of claim 14, wherein the optical calibration signal includes a reference intensity spectrum.

21. The instrumentation of claim 20, wherein a halogen lamp provides the reference intensity spectrum.

22. The instrumentation of claim 14, wherein the optical calibration signal includes reference wavelengths and reference intensity spectra.

23. The instrumentation of claim 14, further including:
   a plurality of probehead assemblies, each coupled to a separate collection optical fiber associated with a different sample or portion thereof; and
   a plurality of calibration optical fibers, each having one end for receiving the calibration signal.

24. The instrumentation of claim 14, wherein:
   the source of excitation is a laser having a nominal wavelength; and
   a plurality of probehead assemblies, at least one of which is used for receiving wavelengths scattered by a reference substance used to calibrate the laser.

25. The instrumentation of claim 24, wherein the substance used to calibrate the laser is cyclohexane.

26. A method of calibrating an optical probe, comprising the steps of:
   illuminating a sample to induce an optical spectrum therefrom;
   providing an optical collection fiber having a first end to receive the optical spectrum and a second end coupled to spectral analysis means;
   providing an optical calibration signal;
   delivering the optical calibration signal to the first end of the optical collection fiber through a calibration fiber;
   directing the optical calibration signal into the first end of the collection fiber; and
   receiving both the optical spectrum and the calibration signal at the spectral analysis means through the collection fiber.

27. The method of claim 26, wherein the optical calibration signal is provided at the location of the spectral analysis means.

28. The method of claim 26, wherein the optical spectrum is representative of a Raman spectrum.

29. The method of claim 26, wherein the optical spectrum is representative of a fluorescence spectrum.

30. The method of claim 26, wherein the step of providing an optical calibration signal includes providing light at a predetermined wavelength.

31. The method of claim 30, wherein the light includes neon light.

32. The method of claim 26, wherein the step of providing an optical calibration signal includes providing light at a predetermined spectral intensity profile.

33. The method of claim 32, wherein the light is from a tungsten halogen source.

34. The method of claim 26, further including the step of illuminating and receiving wavelengths from a reference substance used to calibrate the laser wavelength.

35. The method of claim 34, wherein the reference substance is cyclohexane.

* * * * *